United States Patent
Kanebako

(10) Patent No.: US 8,545,381 B2
(45) Date of Patent: Oct. 1, 2013

(54) AUXILIARY ARTIFICIAL HEART PUMP DRIVE DEVICE AND AUXILIARY ARTIFICIAL HEART SYSTEM

(75) Inventor: Hideki Kanebako, Nagano (JP)

(73) Assignee: Sun Medical technology Research Corporation, Nagano (JP)

( * ) Notice: Subject to any disclaimer, the term of this patent is extended or adjusted under 35 U.S.C. 154(b) by 220 days.

(21) Appl. No.: 12/934,074

(22) PCT Filed: Mar. 22, 2009

(86) PCT No.: PCT/JP2009/055538
§ 371 (c)(1),
(2), (4) Date: Sep. 23, 2010

(87) PCT Pub. No.: WO2009/119462
PCT Pub. Date: Oct. 1, 2009

(65) Prior Publication Data
US 2011/0015732 A1    Jan. 20, 2011

(30) Foreign Application Priority Data
Mar. 25, 2008    (JP) .................................. 2008-077953

(51) Int. Cl.
*A61M 1/10*    (2006.01)

(52) U.S. Cl.
USPC .......................................................... 600/16

(58) Field of Classification Search
USPC ..................................................... 600/16–18
See application file for complete search history.

(56) References Cited

U.S. PATENT DOCUMENTS

| 5,613,935 A | | 3/1997 | Jarvik |
| 5,674,281 A | * | 10/1997 | Snyder .......................... 623/3.28 |
| 6,123,726 A | | 9/2000 | Mori et al. |
| 6,158,553 A | | 12/2000 | Oshima et al. |
| 7,887,479 B2 | * | 2/2011 | LaRose et al. ................... 600/16 |
| 2001/0003802 A1 | * | 6/2001 | Vitale ........................... 623/3.11 |
| 2003/0069465 A1 | * | 4/2003 | Benkowski et al. ............ 600/16 |
| 2007/0055908 A1 | | 3/2007 | Kubo et al. |

FOREIGN PATENT DOCUMENTS

| JP | 07-143604 A | 6/1995 |
| JP | 07-231697 A | 8/1995 |
| JP | 09-266636 A | 10/1997 |
| JP | 09-275699 A | 10/1997 |
| JP | 10085322 A | 4/1998 |
| JP | 2000004600 A | 1/2000 |
| JP | 2007083887 A | 4/2007 |

OTHER PUBLICATIONS

ISR for PCT/JP2009/055538 mailed Apr. 21, 2009.
Ertugrul, N., Fault Tolerant Motor Drive System with Redundancy for Critical Applications, IEEE Power Electronics Specialists Conference, 2002, p. 1457-1462.

* cited by examiner

*Primary Examiner* — Allen Porter, Jr.
(74) *Attorney, Agent, or Firm* — Lowe, Hauptman & Ham

(57) ABSTRACT

An auxiliary artificial heart pump drive device for driving an auxiliary artificial heart pump includes first and second pump control parts which are arranged in duplexed configuration. Each pump control part controls the auxiliary artificial heart pump by outputting a drive signal to the auxiliary artificial heart pump. Each pump control part has a means which, when a failure is detected in the pump control part, electrically cuts off a path through which the drive signal is outputted to the auxiliary artificial heart pump. According to the present invention, it is possible to provide an auxiliary artificial heart pump drive device and an auxiliary artificial heart system which exhibit high availability even when a serious failure occurs by any chance without duplexing a pump device.

7 Claims, 9 Drawing Sheets

| state of first pump control part | first pump control part | | second pump control part | |
|---|---|---|---|---|
| | first power source switch | first switch circuit | second power source switch | second switch circuit |
| normal state | ON | ON | OFF | OFF |
| failure state | OFF | OFF | ON | ON |

AUXILIARY ARTIFICIAL HEART PUMP DRIVE DEVICE AND AUXILIARY ARTIFICIAL HEART SYSTEM

RELATED APPLICATIONS

The present application is national phase of International Application Number PCT/JP2009/055538 filed Mar. 22, 2009, and claims priority from, Japanese Application Number 2008-077953 filed Mar. 25, 2008.

TECHNICAL FIELD

The present invention relates to an auxiliary artificial heart pump drive device and an auxiliary artificial heart system which uses the auxiliary artificial heart pump drive device.

BACKGROUND OF THE INVENTION

Along with the progress of medical technology in recent years, the number of cases where cardiopathy which has been considered as a serious disease can be cured is increased. On the other hand, with respect to serious cardiopathy, at present, there may be also a case where the only way to cure such cardiopathy is the heart transplantation. Under such circumstances, a heart transplantation waiting patient has to wait for a donor who is compatible with the patient. Accordingly, there has been also a case where the heart transplantation cannot be promptly carried out so that the life support of the heart transplantation waiting patient is heavily hindered.

To cope with such a situation, there has been adopted a method in which an auxiliary artificial heart is embedded in such a heart transplantation waiting patient so as to assist the circulation of blood of the patient thus allowing the heart transplantation waiting patient to wait for a donor who is compatible with the patient for a long period. It is expected that the life of a patient which suffers from serious cardiopathy is helped not by a heart of a donor but by an artificial heart in future.

Such an auxiliary artificial heart includes an auxiliary artificial heart pump which functions as a blood pump for assisting functions of a left ventricle and a right ventricle. The auxiliary artificial heart is a so-called life support device and hence, the auxiliary artificial heart pump and an auxiliary artificial heart pump drive device for driving the auxiliary artificial heart pump are requested to exhibit extremely high reliability and availability.

Techniques which are applicable to enhance the reliability and availability of the auxiliary artificial heart pump drive device are disclosed in patent document 1, patent document 2, patent document 3 and non-patent document 1, for example. Patent document 1 discloses an inverter device for driving an AC motor in which control parts are duplexed and the control parts are changed over so as to prevent the flow of an overcurrent. Patent document 2 discloses an electric vehicle control device in which microprocessors which perform a vehicle control are provided doubly, and arithmetic calculation results of the respective microprocessors are checked doubly thus outputting a normal arithmetic calculation result. Patent document 3 discloses a technique relating to a motor drive circuit which includes a main drive circuit and a backup drive circuit for driving a motor, and outputs a drive signal of either one of the main drive circuit and the backup drive circuit to a motor using a switching circuit when a failure is detected in the main drive circuit. Non-patent document 1 discloses a redundant motor which includes motor windings of two systems in the motor.

Patent document 1: JP-A-7-231697
Patent document 2: JP-A-7-143604
Patent document 3: JP-A-2007-83887
Non-patent document: N. Ertugrul, W. Soong, G. Dostal and D. Saxon, "Fault Tolerant Motor Drive System with Redundancy for Critical Application", IEEE Power Electronics Specialists Conference, 2002, p. 1457-1462

DISCLOSURE OF THE INVENTION

Task to be Solved by the Invention

Even when an attempt to enhance availability is made by using one control part constantly and by using the other control part in a standby state as a backup at the time of the occurrence of a failure, in the techniques disclosed in patent document 1, patent document 2 and patent document 3, for example, a power amplifying circuit which supplies a drive power source to the motor is used in common by the control parts. Accordingly, there arises a drawback that when a failure occurs in the power amplifying circuit, the driving of an auxiliary artificial heart pump becomes uncontrollable so that the reliability of an auxiliary artificial heart is lowered and also the availability of the auxiliary artificial heart is not enhanced. Further, in the technique disclosed in non-patent document 1, for example, it is necessary to multiplex a motor side and hence, an auxiliary artificial heart pump becomes large-sized thus making the application of this technique to the auxiliary artificial heart pump substantially impossible.

In this manner, with the mere technique where the circuits are simply connected with each other in parallel as in the case of the prior art, there exists a possibility that the circuit of a back-up-side system is affected by the circuit of the failure system so that the circuit of the back-up-side system does not function normally.

The present invention has been made in view of the above-mentioned technical drawbacks, and it is an object of the present invention to provide an auxiliary artificial heart pump drive device and an auxiliary artificial heart system which exhibit high availability even when a serious failure occurs by any chance without duplexing a pump device.

Means for Solving the Task

To overcome the above-mentioned drawbacks, the present invention provides an auxiliary artificial heart pump drive device for driving an auxiliary artificial heart pump which includes first and second pump control parts arranged in duplexed configuration, and each pump control part controls the auxiliary artificial heart pump by outputting a drive signal to the auxiliary artificial heart pump. Each pump control part also has a means which, when a failure is detected in the pump control part, electrically cuts off a path through which the drive signal is outputted to the auxiliary artificial heart pump.

According to the present invention, even when a failure occurs in the first or second pump control part, the failure which occurs in one pump control part does not influence the other pump control part. Accordingly, the auxiliary artificial heart pump drive device can continue the driving of the auxiliary artificial heart pump while maintaining a normal operation state thus realizing high availability. For example, when a failure occurs in one pump control part (for example, the first pump control part) not only in an open mode but also in a short-circuiting mode, it is possible to prevent the occurrence of a state where an output line of the other pump control part (for example, the second pump control part) is fixed to a ground level so that the other pump control part (for example, the second pump control part) cannot perform a drive control of the auxiliary artificial heart pump.

Further, in the auxiliary artificial heart pump drive device according to the present invention, each pump control part may have a means which stops the supply of electricity to the pump control part when a failure is detected in the pump control part.

According to the present invention, since the supply of electricity to the pump control part is stopped when a failure is detected in the pump control part, even when a failure occurs in the first or second pump control part, it is possible to surely prevent the failure in one pump control part from influencing the other pump control part so that the auxiliary artificial heart pump can be continuously driven thus further enhancing availability of the auxiliary artificial heart pump drive device.

Further, in the auxiliary artificial heart pump drive device according to the present invention, the means which stops the supply of electricity may be a unidirectional switch circuit which is connected to a power source line which supplies electricity to the auxiliary artificial heart pump drive device.

According to the present invention, the constitution of the auxiliary artificial heart pump drive device can be simplified without adopting the complicated constitution and hence, it is possible to enhance the availability of the auxiliary artificial heart pump drive device without lowering the reliability of the auxiliary artificial heart pump drive device.

Further, in the auxiliary artificial heart pump drive device according to the present invention, the unidirectional switch circuit may be constituted of a metal oxide film semiconductor field effect transistor.

According to the present invention, since the semiconductor switch realized by the metal oxide film semiconductor field effect transistor is adopted as the unidirectional switch circuit, even when a failure occurs in the semiconductor switch per se by any chance, most of the failure is a failure in a short-circuiting mode whereby unless double failures consisting of this failure and a failure in the pump control part occur, the failure does not influence the driving of the auxiliary artificial heart pump so that the reliability of the auxiliary artificial heart pump drive device can be remarkably enhanced.

Further, in the auxiliary artificial heart pump drive device according to the present invention, each pump control part may include a power amplifier which amplifies power of the drive signal and a bidirectional switch circuit which is provided between an output of the power amplifier and the auxiliary artificial heart pump, and when the first pump control part is in a normal state, the bidirectional switch circuit of the first pump control part may be set in a conductive state and the bidirectional switch circuit of the second pump control part may be set in a cut-off state, and when the first pump control part is in a failure state, the bidirectional switch circuit of the first pump control part may be set in a cut-off state and the bidirectional switch circuit of the second pump control part may be set in a conductive state.

According to the present invention, the constitution of the auxiliary artificial heart pump drive device can be simplified without adopting the complicated constitution and hence, it is possible to enhance the availability of the auxiliary artificial heart pump drive device without lowering the reliability of the auxiliary artificial heart pump drive device.

Further, in the auxiliary artificial heart pump drive device according to the present invention, the power amplifier may be an inverter circuit.

According to the present invention, the constitution of the auxiliary artificial heart pump drive device can be simplified and, further, even when a failure occurs by any chance, most of the failure is a failure in a short-circuiting mode and hence, unless double failures occur, the auxiliary artificial heart pump drive device can continue driving of the auxiliary artificial heart pump while maintaining a normal operation state thus acquiring high availability.

Further, in the auxiliary artificial heart pump drive device according to the present invention, the bidirectional switch circuit may be constituted of a metal oxide film semiconductor field effect transistor.

According to the present invention, since the semiconductor switch realized by the metal oxide film semiconductor field effect transistor is adopted as the bidirectional switch circuit, even when a failure occurs in the semiconductor switch per se by any chance, most of the failure is a failure in a short-circuiting mode whereby unless double failures occur, the failure does not influence the driving of the auxiliary artificial heart pump thus largely enhancing the reliability of the auxiliary artificial heart pump drive device.

In the auxiliary artificial heart pump drive device according to the present invention, each pump control part includes a detection circuit for detecting a failure in the pump control part, and can electrically cut off a path through which the drive signal is outputted to the auxiliary artificial heart pump from the pump control part when the failure in the pump control part is detected by the detection circuit.

According to the present invention, it is possible to provide the auxiliary artificial heart pump drive device having high availability even when a serious failure occurs by any chance without duplexing the pump device.

Further, in the auxiliary artificial heart pump drive device according to the present invention, the detection circuit can detect a failure in the pump control part using at least one monitoring result out of an overcurrent of a power source line for supplying electricity to the auxiliary artificial heart pump drive device, an overvoltage of the power source line and a temperature near the pump control part.

According to the present invention, an estimated failure factor is monitored, and when a failure is detected by any chance, the switching of the system is rapidly performed thus providing the auxiliary artificial heart pump drive device which exhibits high reliability and high availability.

Further, in the auxiliary artificial heart pump drive device according to the present invention, assuming a detection period for detecting the presence or non-presence of a failure based on the overcurrent of the power source line as $T1$, a detection period for detecting the presence or non-presence of a failure based on the overvoltage of the power source line as $T2$, and a detection period for detecting the presence or non-presence of a failure based on the temperature near the pump control part as $T3$, the detection periods may satisfy the relationship of $T1<T2<T3$.

According to the present invention, by performing the failure determination such that the detection period for detecting the overcurrent becomes shortest among three kinds of detection periods, the system can be rapidly switched with respect to the failure factor which is difficult to avoid and is more serious thus enhancing the availability of the auxiliary artificial heart pump drive device. Further, by performing the failure determination such that the detection period for detecting the temperature near the pump control part becomes longest among three kinds of detection periods, with respect to the countermeasure against the failure factor which brings about a serious failure when the failure occurs but has a long cycle of change, the order of priority assigned to the failure factor is lowered so that the auxiliary artificial heart pump drive device can rapidly cope with other failure factors thus enhancing the availability of the auxiliary artificial heart pump drive device.

Further, the present invention relates to an auxiliary artificial heart system for assisting the flow of blood in a heart, wherein the auxiliary artificial heart system includes an auxiliary artificial heart pump, and any one of the above-mentioned auxiliary artificial heart pump drive devices for driving the auxiliary artificial heart pump.

According to the present invention, it is possible to provide an auxiliary artificial heart system which exhibits high availability even when a serious failure occurs by any chance without duplexing the pump device.

BRIEF DESCRIPTIONS OF THE DRAWINGS

BEST MODE FOR CARRYING OUT THE INVENTION

Hereinafter, an embodiment of the present invention is explained in detail in conjunction with drawings. The embodiment explained hereinafter does not unduly limit contents of the present invention described in Claims. Further, all constitutions explained hereinafter do not always constitute inevitable constitutional elements of the present invention.

Figure 1:
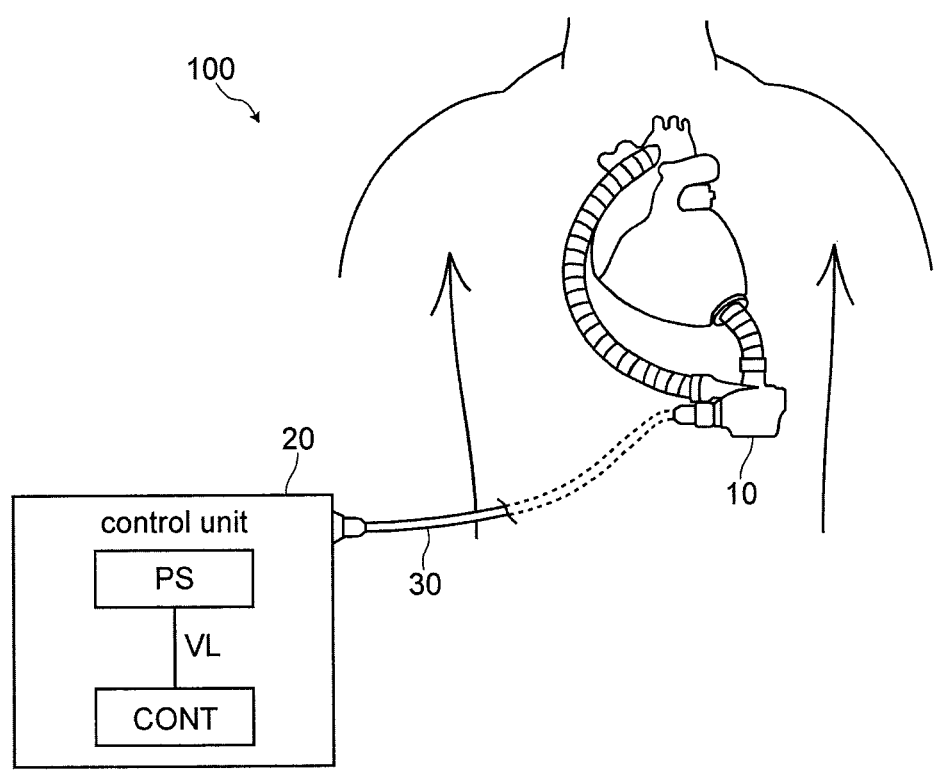
FIG. 1 is a view showing a constitutional example of an auxiliary artificial heart system according to an embodiment of the present invention.

FIG. 1 shows a constitutional example of an auxiliary artificial heart system according to an embodiment of the present invention.

The auxiliary artificial heart system (a pump system, a motor system in broad meaning) 100 according to this embodiment includes an auxiliary artificial heart pump (a pump, a motor in broad meaning) 10 and a control unit 20. The auxiliary artificial heart pump 10 and the control unit 20 are connected with each other via a cable 30.

The auxiliary artificial heart pump 10 is a blood pump which assists a function of a left ventricle of a heart and is embedded in the inside of a human body. As such an auxiliary artificial heart pump 10, a pulsation-flow-type blood pump which imparts a predetermined cycle to the flow of blood to be circulated may be adopted or a continuous-flow-type blood pump which produces the continuous flow of blood to be circulated may be adopted.

The control unit 20 includes a power source PS and an auxiliary artificial heart pump drive device (a pump drive device, a motor drive device in broad meaning) CONT and is provided outside the body. The power source PS supplies a power source voltage to the auxiliary artificial heart pump drive device CONT from any one of an AC power source, a built-in battery and an emergency battery via a power source line VL. The auxiliary artificial heart pump drive device CONT generates a drive current (a drive signal in broad meaning) which drives the auxiliary artificial heart pump 10 in a state where a power source voltage from the power source PS is supplied. The cable 30 has a signal line through which a drive current for driving the auxiliary artificial heart pump 10 from the control unit 20 is transmitted.

Figure 2:
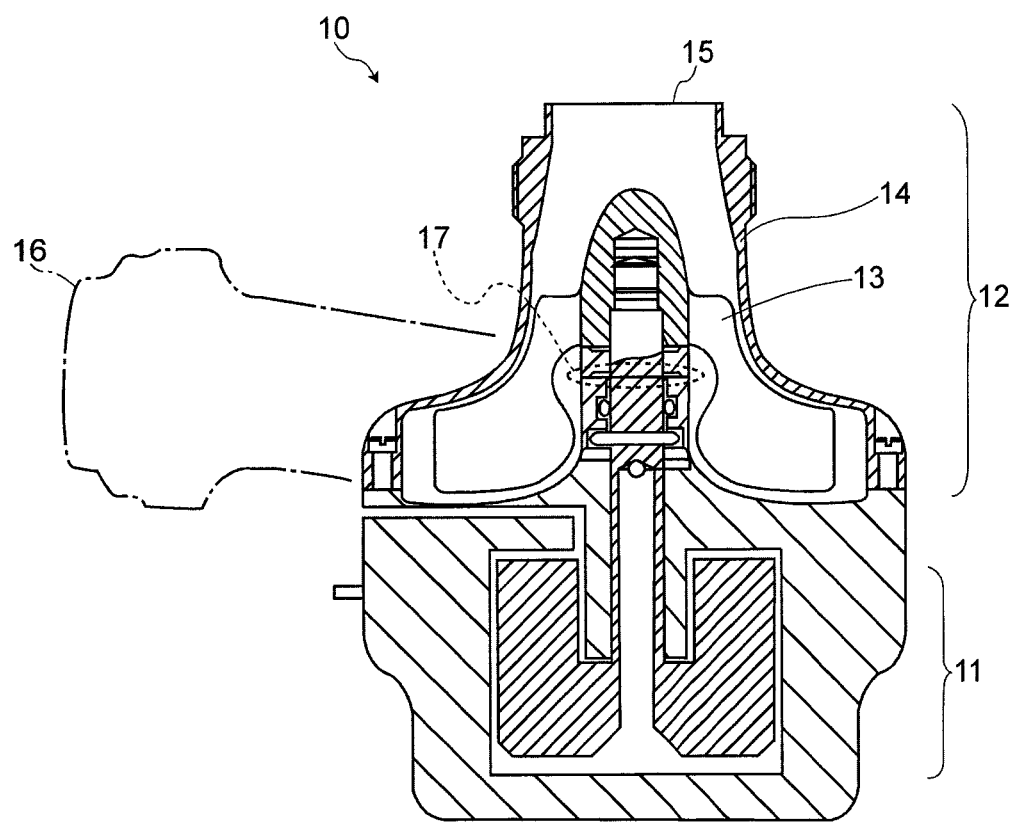
FIG. 2 is a view showing one example of a cross-section of an auxiliary artificial heart pump according to the embodiment.

FIG. 2 shows one example of a cross section of the auxiliary artificial heart pump 10 according to this embodiment. Although FIG. 2 shows a constitutional example of the auxiliary artificial heart pump 10, this embodiment is not limited to the auxiliary artificial heart pump having the constitution shown in FIG. 2.

The auxiliary artificial heart pump 10 includes a drive part 11 which has a cylindrical motor and a pump part 12 which is connected to the drive part 11. The pump part 12 includes an impeller 13 which is driven by way of a rotary shaft of the motor, and a pump casing 14 which is connected to the drive part 11 in a state where the pump casing 14 covers the impeller 13. The auxiliary artificial heart pump 10 is configured such that when blood in a left ventricle of a heart flows into the pump casing 14 via a blood vessel (artificial blood vessel) and an inlet port 15, after flow energy is imparted by the impeller 13, the blood flows out to an aorta via an outlet port 16 formed in a side surface of the pump casing 14 and a blood vessel (artificial blood vessel).

In the auxiliary artificial heart pump 10, a mechanical seal part 17 is arranged between the drive part 11 and the pump part 12. Accordingly, the pump part 12 and the drive part 11 are slidably and firmly sealed from each other thus suppressing leaking of the blood from the pump part 12 to the drive part 11 as much as possible. As a result, the generation of a blood clot is suppressed thus suppressing stopping of an operation of the pump and a change in an operational state of the pump.

The pump part 12 is a centrifugal pump by which a larger blood flow rate can be expected than an axial flow pump, wherein an AC motor can be used as a motor for driving the impeller 13.

When the auxiliary artificial heart pump 10 is constituted as shown in FIG. 2, the control unit 20 shown in FIG. 1 further has a means for circulating a cool sealing liquid which suppress the coagulation of blood in the mechanical seal part and the generation of heat in the drive part 11 and the motor part 12. In this case, a circulation passage for the cool sealing liquid is formed by way of the cable 30.

Such an auxiliary artificial heart system 100 is, since it is always necessary to circulate blood by the auxiliary artificial heart pump 10, requested to exhibit both high reliability and high availability. Accordingly, not only the auxiliary artificial heart pump 10 is requested to exhibit reliability and availability, but also the auxiliary artificial heart pump drive device CONT which constitutes the control unit 20 is requested to exhibit reliability and availability. In view of such a circumstance, this embodiment provides an auxiliary artificial heart pump drive device CONT which provides high availability by continuing a pump operation of the auxiliary artificial heart pump 10 even when a serious failure occurs due to a failure in the auxiliary artificial heart pump drive device CONT or the like.

Figure 3:
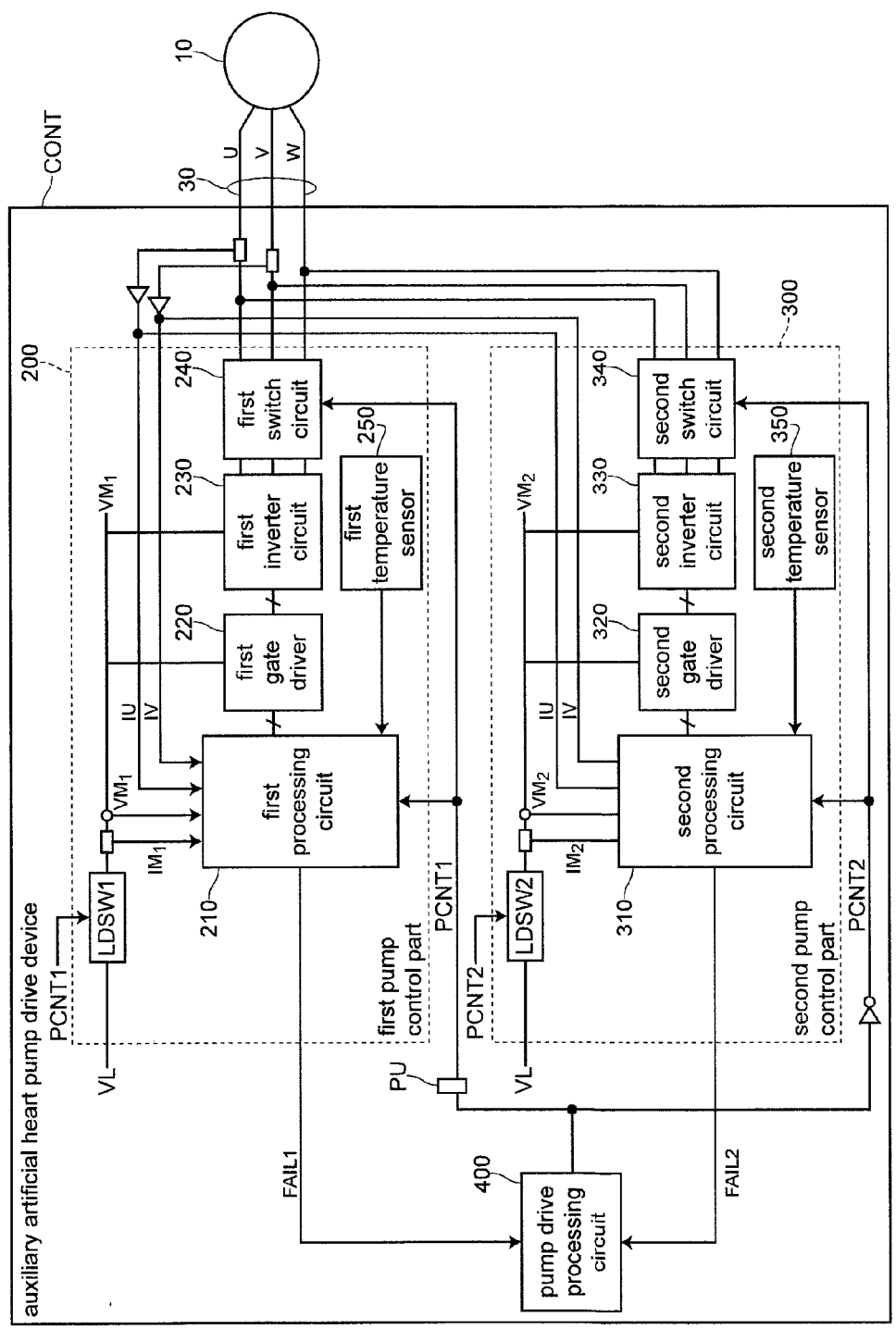
FIG. 3 is a block diagram showing a constitutional example of an auxiliary artificial heart pump drive device in a control unit according to the embodiment.

FIG. 3 is a block diagram of a constitutional example of the auxiliary artificial heart pump drive device CONT of the control unit 20 according to this embodiment. In FIG. 3, parts identical with the parts shown in FIG. 1 are given same symbols and the explanation of these parts is omitted when appropriate.

In FIG. 3, the auxiliary artificial heart pump 10 includes a 3-phase AC motor driven by a three-phase drive current. The auxiliary artificial heart pump drive device CONT generates a 3-phase (U phase, V phase, W phase) drive current (drive signal in broad meaning) for the auxiliary artificial heart pump 10, and controls driving of the auxiliary artificial heart pump 10. To be more specific, the auxiliary artificial heart pump drive device CONT includes first and second pump control parts 200, 300 arranged in duplexed configuration, wherein each pump control part generates a three-phase drive current for the auxiliary artificial heart pump 10 and controls the driving of the auxiliary artificial heart pump 10. Here, the first pump control part 200 is connected with an output signal line which outputs a drive current to the auxiliary artificial heart pump 10, the second pump control part 300 is connected to an output signal line which outputs a drive current to the auxiliary artificial heart pump 10, and the drive current which is generated by either one of the pump control parts is supplied to the auxiliary artificial heart pump 10.

The auxiliary artificial heart pump drive device CONT includes a pump drive processing circuit 400, and the pump drive processing circuit 400 controls the first and second pump control parts (first and second motor control parts in broad meaning) 200, 300 having the above-mentioned constitution.

The first pump control part 200, in a normal state, functions as a pump control part of a main system which controls the driving of the auxiliary artificial heart pump 10 by generating a three-phase drive current for the auxiliary artificial heart pump 10. On the other hand, the second pump control part 300, in a failure state where a failure is detected in the first pump control part 200, functions as a pump control part of a backup system which controls the driving of the auxiliary artificial heart pump 10 by generating a three-phase drive current for the auxiliary artificial heart pump 10.

The first pump control part 200 includes a first processing circuit (first detection circuit) 210, a first gate driver 220, a first inverter circuit (power amplifier) 230, a first switch circuit 240, a first temperature sensor 250, and a first power source switch LDSW1.

To the first processing circuit 210, the first gate driver 220 and the first inverter circuit 230, as a power source voltage, a voltage supplied to a power source line VL is supplied via the first power source switch LDSW1. Further, a first pump drive control signal PCNT1 is supplied to the first processing circuit 210 and the first switch circuit 240, and operations of these circuits are controlled in response to the first pump drive control signal PCNT1.

The first processing circuit 210 detects the presence or non-presence of a failure in the first pump control part 200. To be more specific, the first processing circuit 210 detects the presence or non-presence of a failure in the first pump control part 200 based on at least one monitored result among a voltage $VM_1$ of the power source line VL, a current $IM_1$ of the power source line VL and a sensing result of a first temperature sensor 250 supplied to the first pump control part 200. For example, when it is detected that the voltage $VM_1$ exceeds a predetermined threshold value for a predetermined period based on the result of monitoring the voltage $VM_1$ of the power source line VL, the first processing circuit 210 determines that the voltage of the power source line VL is an overvoltage thus detecting a failure in the first processing circuit 210. Further, for example, when it is detected that the current $IM_1$ exceeds a predetermined threshold value for a predetermined period based on the result of monitoring the current $IM_1$ of the power source line VL, the first processing circuit 210 determines that the current of the power source line VL is an overcurrent thus detecting a failure in the first processing circuit 210. Still further, for example, when it is detected that a temperature detected by the first temperature sensor 250 exceeds a predetermined threshold value for a predetermined period based on a sensing result of the first temperature sensor 250, the first processing circuit 210 detects a failure in the first processing circuit 210.

A detection result of the first processing circuit 210 is outputted to the pump drive processing circuit 400 as a detection signal FAIL1. The pump drive processing circuit 400 outputs a first pump drive control signal PCNT1 to the first pump control part 200 thus performing a control of operating or stopping the first pump control part 200.

Further, the first processing circuit 210 is configured to generate a pulse width modulation (PWM) signal and to output the signal to the first gate driver 220. To be more specific, the first processing circuit 210 monitors amplitudes and phases of a drive current IU (U-phase drive current) and IV (V-phase drive current) for the auxiliary artificial heart pump 10, and generates a PWM signal for controlling amplitudes and phases of three-phase drive current to be outputted by changing pulse widths of the drive currents in response to the monitored amplitudes and phases.

The first gate driver 220, upon receiving the PWM signal from the first processing circuit 210, generates a gate signal for a first inverter circuit 230 for amplifying the drive current for the auxiliary artificial heart pump 10. The first inverter circuit 230 generates the three-phase drive current which is amplified based on the gate signal from the first gate driver 220. To suppress a penetration current at the time of performing a power amplifying operation in the first inverter circuit 230, in response to the PWM signal, the first gate driver 220 generates gate signals whose change timings do not agree with each other such that fall timing at which a power level is shifted from H level to L level and rise timing at which a power level is shifted from L level to H level from do not take place simultaneously.

The first switch circuit 240, based on the first pump drive control signal PCNT1, electrically connects signal lines through which the three-phase drive current amplified by the first inverter circuit 230 are supplied with motor wirings of the auxiliary artificial heart pump 10 or cuts off such an electrical connection. That is, the first pump control part 200 includes a means which electrically cuts off a path through which the three-phase drive current is outputted to the auxiliary artificial heart pump 10, and electrically cuts off the path in response to the first pump drive control signal PCNT1 when a failure is detected in the first processing circuit 210.

The first temperature sensor 250 detects a temperature near the first pump control part 200. To be more specific, the first temperature sensor 250 detects the temperature near the first inverter circuit 230. A detection result of the first temperature sensor 250 is notified to the first processing circuit 210.

The first power source switch LDSW1 has one end thereof electrically connected to the power source line VL and the other end thereof electrically connected to the first processing circuit 210, the first gate driver 220 and the first inverter circuit 230 which constitute the first pump control part 200. Then, a voltage of the power source line VL is supplied as a power source voltage for the first processing circuit 210, the first gate driver 220 and the first inverter circuit 230 which constitute the first pump control part 200 via the first power source switch LDSW1. The first power source switch LDSW1 is subject to an ON/OFF control in response to the first pump drive control signal PCNT1.

The second pump control part 300 includes a second processing circuit (second detection circuit) 310, a second gate driver 320, a second inverter circuit (power amplifier) 330, a second switch circuit 340, a second temperature sensor 350, and a second power source switch LDSW2.

To the second processing circuit 310, the second gate driver 320 and the second inverter circuit 330, as a power source voltage, a voltage supplied to a power source line VL is supplied via the second power source switch LDSW2. Further, a second pump drive control signal PCNT2 is supplied to the second processing circuit 310 and the second switch circuit 340, and operations of these circuits are controlled in response to the second pump drive control signal PCNT2.

The second processing circuit 310 detects the presence or non-presence of a failure in the second pump control part 300. To be more specific, the second processing circuit 310 detects the presence or non-presence of a failure in the second pump control part 300 based on at least one monitored result among a voltage $VM_2$ of the power source line VL, a current $IM_2$ of the power source line VL and a sensing result of a second temperature sensor 350 supplied to the second pump control part 300. For example, when it is detected that the voltage $VM_2$ exceeds a predetermined threshold value for a predetermined period based on the result of monitoring the voltage $VM_2$ of the power source line VL, the second processing circuit 310 determines that the voltage of the power source line VL is an overvoltage thus detecting a failure in the second processing circuit 310. Further, for example, when it is detected that the current $IM_2$ exceeds a predetermined threshold value for a predetermined period based on the result of monitoring the current $IM_2$ of the power source line VL, the second processing circuit 310 determines that the current of the power source line VL is an overcurrent thus detecting a failure in the second processing circuit 310. Still further, for example, when it is detected that a temperature detected by the second temperature sensor 350 exceeds a predetermined threshold value for a predetermined period based on a sensing result of the second temperature sensor 350, the second processing circuit 310 detects a failure in the second processing circuit 310.

A detection result of the second processing circuit 310 is outputted to the pump drive processing circuit 400 as a detection signal FAIL2. The pump drive processing circuit 400 outputs a first pump drive control signal PCNT1 thus performing a control for operating or stopping the second pump control part 300 in response to the second pump drive control signal PCNT2 which is a signal reversed from the first pump drive control signal PCNT1.

Further, the second processing circuit 310 is configured to generate a PWM signal and to output the signal to the second gate driver 320. To be more specific, the second processing circuit 310 monitors amplitudes and phases of a drive current IU (U-phase drive current) and IV (V-phase drive current) for the auxiliary artificial heart pump 10, and generates a PWM signal for controlling amplitudes and phases of three-phase drive current to be outputted in response to the monitored pulse widths.

The second gate driver 320, upon receiving the PWM signal from the second processing circuit 310, generates a gate signal for a second inverter circuit 330 for amplifying the drive current for the auxiliary artificial heart pump 10. The second inverter circuit 330 generates the three-phase drive current which is amplified based on the gate signal from the second gate driver 320. To suppress a penetration current at the time of performing a power amplifying operation in the second inverter circuit 330, in response to the PWM signal, the second gate driver 320 generates gate signals whose change timing do not agree with each other such that fall timing at which a power level is shifted from H level to L level and rise timing at which a power level is shifted from L level to H level do not take place simultaneously.

The second switch circuit 340, based on the second pump drive control signal PCNT2, electrically connects signal lines through which the three-phase drive current amplified by the second inverter circuit 330 are supplied with motor wirings of the auxiliary artificial heart pump 10 or cuts off such an electrical connection. That is, the second pump control part 300 includes a means which electrically cuts off a path through which the three-phase drive current is outputted to the auxiliary artificial heart pump 10, and electrically cuts off the path in response to the second pump drive control signal PCNT2 when a failure is detected in the second processing circuit 310.

The second temperature sensor 350 detects a temperature near the second pump control part 300. To be more specific, the second temperature sensor 350 detects the temperature near the second inverter circuit 330. A detection result of the second temperature sensor 350 is notified to the second processing circuit 310.

The second power source switch LDSW2 has one end thereof electrically connected to the power source line VL and the other end thereof electrically connected to the second processing circuit 310, the second gate driver 320 and the second inverter circuit 330 which constitute the second pump control part 300. Then, a voltage of the power source line VL is supplied as a power source voltage for the second processing circuit 310, the second gate driver 320 and the second inverter circuit 330 which constitute the second pump control part 300 via the second power source switch LDSW2. The second power source switch LDSW2 is subject to an ON/OFF control in response to the second pump drive control signal PCNT2.

A signal line through which the first pump drive control signal PCNT1 is transmitted is pulled up so that the first pump drive control signal PCNT1 at H level is transmitted to the first pump control part 200 unless the pump drive processing circuit 400 outputs the first pump drive control signal PCNT1 at L level. Accordingly, in an initial state, the first pump drive control signal PCNT1 assumes H level and the second pump drive control signal PCNT2 assumes L level. Accordingly, the first power source switch LDSW1 is turned on so that electricity is supplied to respective parts of the first pump control part 200, while the second power source switch LDSW2 is turned off so that operations of the respective parts of the second pump control part 300 are stopped. Then, when a failure in the first pump control part 200 is detected in response to the detection signal FAIL1, the pump drive processing circuit 400 sets the first pump drive control signal PCNT1 at L level. Accordingly, the second pump drive control signal PCNT2 assumes H level so that the first power source switch LDSW1 is turned off whereby the operations of the respective parts of the first pump control part 200 are stopped, and the second power source switch LDSW2 is turned on whereby electricity is supplied to the respective parts of the second pump control part 300 so that these parts are operated.

When a failure in the first pump control part 200 is detected in response to the detection signal FAIL1, the pump drive processing circuit 400 notifies an alarm state to the outside and urges the replacement of the control unit 20 (auxiliary artificial heart pump drive device CONT). The second pump control part 300 continues the driving of the auxiliary artificial heart pump while maintaining a normal operation state until the control unit 20 is replaced. Further, when a failure in the second pump control part 300 is detected in response, to a detection signal FAIL2 by any chance, the pump drive processing circuit 400 operates so as to continue the driving of the auxiliary artificial heart pump as much as possible by performing processing such as the lowering of a pump drive rotational speed, for example.

In this manner, the first pump control part 200 may include a first switch circuit 240 as a means which electrically cuts off a path through which a drive signal is outputted to the auxiliary artificial heart pump 10 when a failure is detected in the first pump control part 200. Further, the second pump control part 300 may include a second switch circuit 340 as a means which electrically cuts off a path through which a drive signal is outputted to the auxiliary artificial heart pump 10 when a failure is detected in the second pump control part 300.

Due to such a constitution, even when a failure occurs in the first or second pump control part 200, 300, the failure in one pump control part does not influence the other pump control part and hence, the auxiliary artificial heart pump drive device can continue the driving auxiliary artificial heart pump 10 while maintaining a normal operation state. Particularly, as a failure mode of the first or second pump control part 200, 300, an open mode where an output or an inner node of the first or second pump control part 200, 300 assumes a floating state and a short-circuiting mode where a power source line and a ground line are short-circuited to each other are named. Accordingly, this embodiment can avoid the situation where when a failure occurs in one pump control part (for example, the first pump control part 200) in a short-circuiting mode, an output line of the other pump control part (for example, the second pump control part 300) is fixed to a ground level so that the other pump control part (for example, the second pump control part 300) cannot perform a drive control of the auxiliary artificial heart pump 10.

Further, the first pump control part 200 may include the first power source switch LDSW1 as a means which stops the supply of electricity to the first pump control part 200 when a failure is detected in a short-circuiting mode or an open mode in the first pump control part 200. Further, the second pump control part 300 may include the second power source switch LDSW2 as a means which stops the supply of electricity to the second pump control part 300 when a failure is detected in a short-circuiting mode or an open mode in the second pump control part 300.

Due to such a constitution, even when a failure occurs in the first or second pump control part 200, 300, by continuing the driving of the auxiliary artificial heart pump 10 in such a manner that the other pump control part is surely prevented from being influenced by the failure in one pump control part, it is possible to further enhance the availability of the auxiliary artificial heart pump drive device CONT. Also in this case, it is possible to surely avoid a situation where when a failure occurs in one pump control part (for example, the first pump control part 200) in a short-circuiting mode, an output line of the other pump control part (for example, the second pump control part 300) is fixed to a ground level so that the other pump control part (for example, the second pump control part 300) cannot perform a drive control of the auxiliary artificial heart pump 10.

Next, a specific constitutional example of the auxiliary artificial heart pump drive device CONT shown in FIG. 3 which performs a control for enhancing such availability is explained.

Figure 4:
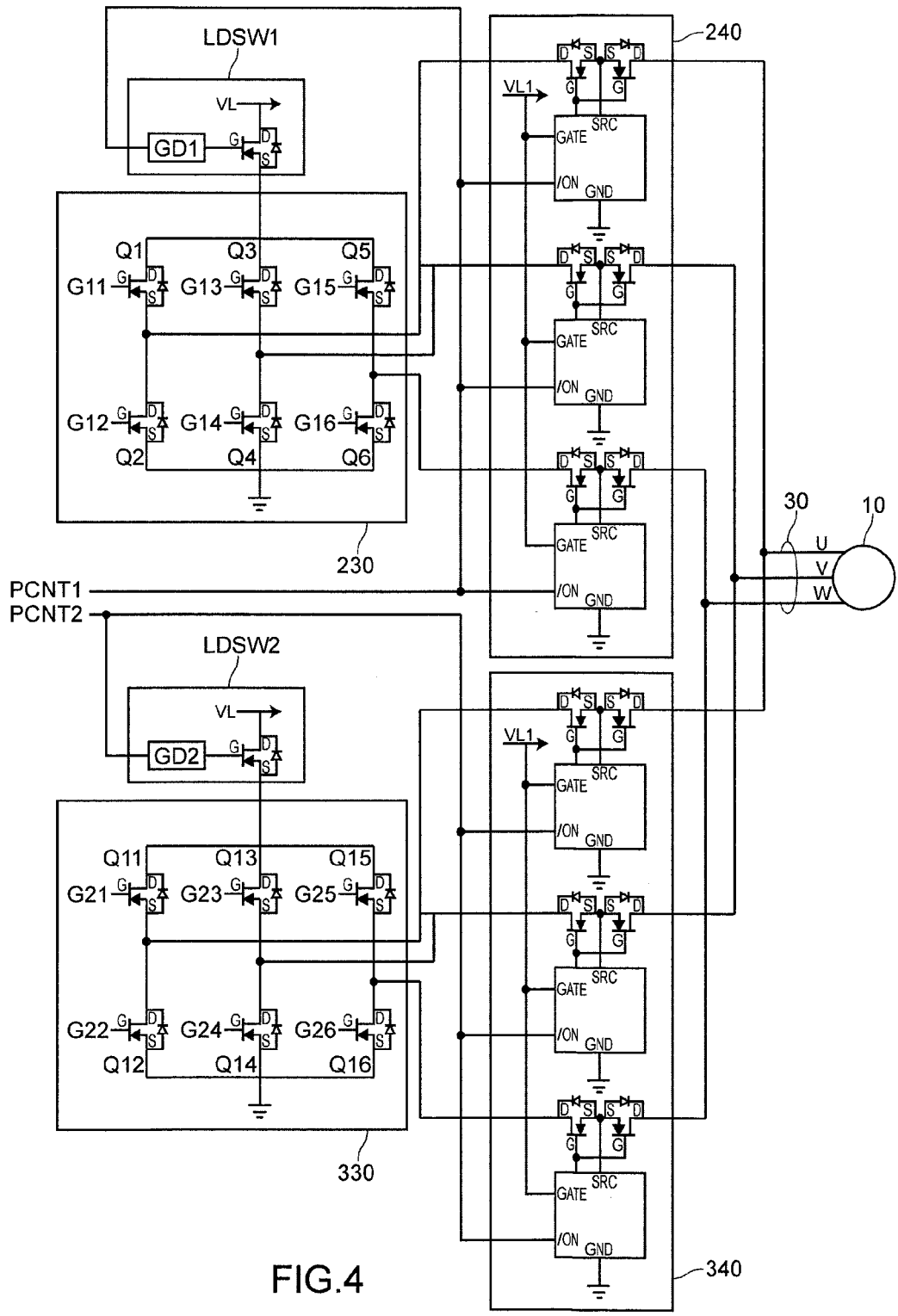
FIG. 4 is a circuit diagram of a constitutional example of first and second inverter circuits, first and second switch circuits and first and second power source switches of the auxiliary artificial heart pump drive device shown in FIG. 3.

FIG. 4 shows a circuit diagram of a constitutional example of the first and second inverter circuits 230, 330, the first and second switch circuits 240, 340 and the first and second power source switches LDSW1, LDSW2 of the auxiliary artificial heart pump drive device CONT shown in FIG. 3. In FIG. 4, parts identical with the parts shown in FIG. 3 are given same symbols and the explanation of these parts is omitted when appropriate.

The first power source switch LDSW1 is a unidirectional switch circuit and is constituted of a metal oxide semiconductor field effect transistor (MOSFET). To be more specific, the MOSFET which has a drain thereof connected to the power source line VL and a source thereof connected to the power source line of the first inverter circuit 230 functions as the first power source switch LDSW1. Further, an anode terminal of a diode element is connected to a source of the MOSFET and a cathode terminal of the diode element is connected to a drain of the MOSFET.

Further, in this embodiment, the first power source switch LDSW1 includes a gate driver GD1, and the gate driver GD1 generates a gate signal for a switch constituted of the MOSFET in response to the first pump drive control signal PCNT1. To be more specific, the gate driver GD1 generates a gate signal for the MOSFET such that the MOSFET assumes a conductive state when a power level of the first pump drive control signal PCNT1 is at H level, and the MOSFET assumes a cut-off state when the power level of the first pump drive control signal PCNT1 is at L level.

The first inverter circuit 230 is constituted such that inverter circuits are provided corresponding to the respective phases of the three-phase drive current. The inverter circuit is constituted by inserting a circuit in which n-type (first conductive type in broad meaning) MOSFETs are connected in series between a ground line and a source of a MOSFET of the first power source switch LDSW1. To be more specific, one inverter circuit includes, corresponding to the U phase, the MOSFET(Q1) in which a gate signal G11 is supplied to a gate and a source of a MOSFET of the first power source switch LDSW1 is connected to a drain, and the MOSFET(Q2) in which a drain is connected to the source of the MOSFET(Q1), a gate signal G12 is supplied to a gate, and a ground line is connected to a source. In the same manner, another inverter circuit includes, corresponding to the V phase, the MOSFET (Q3) in which a gate signal G13 is supplied to a gate and the source of the MOSFET of the first power source switch LDSW1 is connected to a drain, and the MOSFET(Q4) in which a drain is connected to the source of the MOSFET(Q3), a gate signal G14 is supplied to a gate, and a ground line is connected to a source. Further, another inverter circuit includes, corresponding to the W phase, the MOSFET(Q5) in which a gate signal G15 is supplied to a gate and the source of the MOSFET of the first power source switch LDSW1 is connected to a drain, and the MOSFET(Q6) in which a drain is connected to the source of the MOSFET(Q5), a gate signal G16 is supplied to a gate, and a ground line is connected to a source. In the respective MOSFETs (Q1 to Q6) which constitute the first inverter circuit 230, a diode element in the direction shown in FIG. 4 is connected between the source and the drain.

A U-phase drive current is taken out from a connection node between the source of the MOSFET(Q1) and the drain of the MOSFET(Q2). A V-phase drive current is taken out from a connection node between the source of the MOSFET (Q3) and the drain of the MOSFET(Q4). A W-phase drive current is taken out from a connection node between the source of the MOSFET(Q5) and the drain of the MOSFET (Q6).

Figure 5:
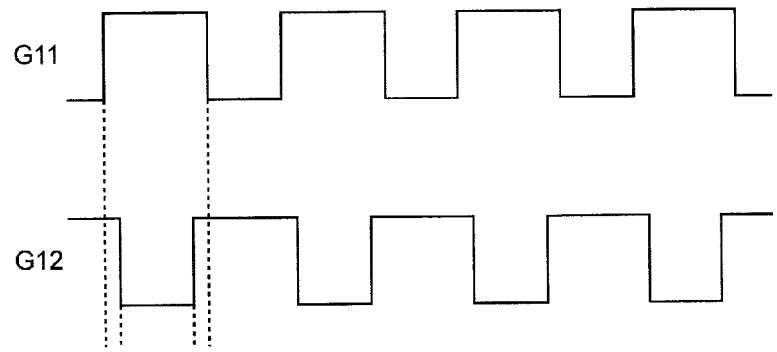
FIG. 5 is an explanatory view of a gate signal of the first inverter circuit shown in FIG. 4.

FIG. 5 is an explanatory view of gate signals in the first inverter circuit 230 shown in FIG. 4. FIG. 5 shows one example of the gate signals G11, G12 for the MOSFETs (Q1, Q2) of the first inverter circuit 230.

As shown in FIG. 5, the first gate driver 220 generates gate signals such that the change timings of the gate signals for the MOSFET which are connected in series do not agree with each other. Due to such an operation, the first inverter circuit 230 can amplify the U-phase drive signal corresponding to the pulse widths of the gate signals G11, G12 without generating a penetration current.

Although the explanation has been made with respect to the gate signals G11, G12 in FIG. 5, the same goes for a V-phase drive current amplified in response to the gate signals G13, G14, and a W-phase drive current amplified in response to the gate signals G15, G16.

The first switch circuit 240 shown in FIG. 4 is constituted of bidirectional switch circuits which are provided corresponding to respective phases of three-phase drive current. The bidirectional switch circuit is constituted of MOSFETs. Further, the first switch circuit 240 includes gate drivers which are provided corresponding to the bidirectional switch circuits of respective phases, and the gate driver generates gate signals of respective MOSFETs which constitute the bidirectional switch circuit.

To be more specific, the bidirectional switch circuit includes two n-type MOSFETs whose sources are connected with each other, wherein a drain of one MOSFET is connected to an output line for a drive current from the first inverter circuit 230 and a drain of the other MOSFET is connected to a motor winding. Here, a common gate signal is supplied to gates of two MOSFETs from the gate driver. Between a source and a drain of each MOSFET, a diode is connected in the direction shown in FIG. 4. The gate driver which is provided corresponding to each bidirectional switch circuit, in a state where a predetermined power source voltage VL1 is supplied to the gate driver, generates a gate signal such that the MOSFETs which constitute the bidirectional switch circuit become conductive with each other when a first pump drive control signal PCNT1 is at H level.

Figure 6:
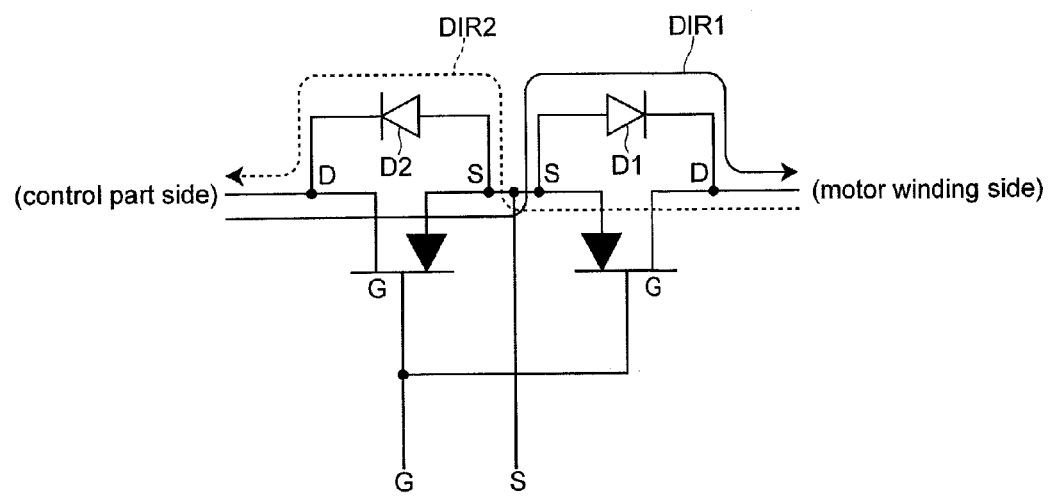
FIG. 6 is a circuit diagram of a constitutional example of a bidirectional switch circuit of the first switch circuit shown in FIG. 4.

FIG. 6 shows a circuit diagram of a constitutional example of the bidirectional switch circuit of the first switch circuit 240 shown in FIG. 4. Although FIG. 6 shows the constitutional example of the bidirectional switch circuit provided corresponding to a U-phase drive signal, the bidirectional switch circuits provided corresponding to drive signals of other phases have the constitutions substantially equal to the constitution shown in FIG. 6.

Figures 7, 8:
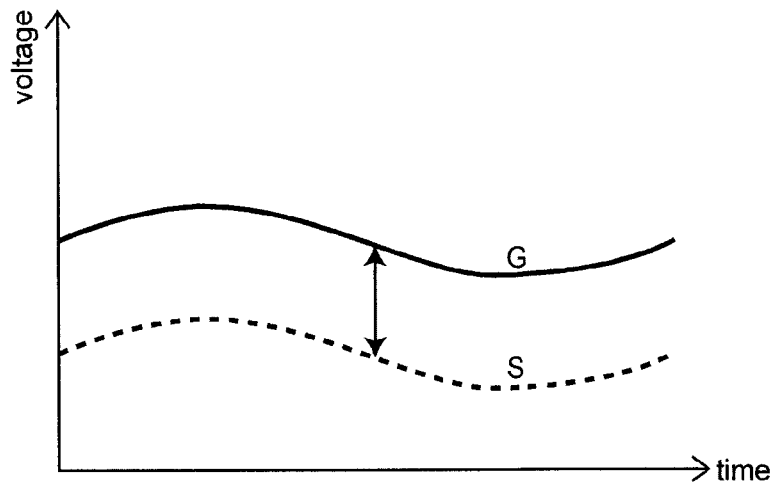
FIG. 7 is an operational explanatory view of a gate driver provided corresponding to the bidirectional switch circuit shown in FIG. 6.
FIG. 8 is an explanatory view of a control example of the first and the second switch circuits and the first and the second power source switches shown in FIG. 4.

FIG. 7 shows an operational explanatory view of the gate driver provided corresponding to the bidirectional switch circuit shown in FIG. 6. Although FIG. 7 shows the operational explanatory view of the gate driver provided corresponding to a U-phase drive signal, the gate drivers provided corresponding to drive signals of other phases are operated in the same manner as shown in FIG. 7.

When a first pump drive control signal PCNT1 is at H level, each gate driver in the first switch circuit 240, as shown in FIG. 7, generates a gate signal such that a gate voltage of the MOSFET has a higher potential than a source voltage and the MOSFET is turned on. As a result, in the bidirectional switch circuit, when a control part side has a higher potential than a motor winding side, a current flows in the direction DIRT along the drain, the source and the diode element D1 of the MOSFET (see FIG. 6), while when the control part side has a lower potential than the motor winding side, a current flows in the direction DIR2 along the drain, the source and the diode element D2 of the MOSFET (see FIG. 6).

Here, when the first pump drive control signal PCNT1 is at L level, each gate driver of the first switch circuit 240 generates a gate signal such that a gate voltage of the MOSFET has a lower potential than a source voltage so that the bidirectional switch circuit can be electrically cut off.

The second power source switch LDSW2 is, in the same manner as the first power source switch LDSW1, a unidirectional switch circuit and is constituted of a MOSFET. To be more specific, the MOSFET which has a drain thereof connected to the power source line VL and a source thereof connected to the power source line of the second inverter circuit 330 functions as the second power source switch LDSW2. Further, an anode terminal of a diode element is connected to a source of the MOSFET and a cathode terminal of the diode element is connected to a drain of the MOSFET.

Further, in this embodiment, the second power source switch LDSW2 includes a gate driver GD2, and the gate driver GD2 generates a gate signal for a switch constituted of the MOSFET in response to the second pump drive control signal PCNT2. To be more specific, the gate driver GD2 generates a gate signal for the MOSFET such that the MOSFET assumes a conductive state when the power level of the second pump drive control signal PCNT2 is at H level, and the MOSFET assumes a cut-off state when the power level of the second pump drive control signal PCNT2 is at L level.

The second inverter circuit 330 is constituted such that inverter circuits are provided corresponding to the respective phases of the three-phase drive current. The inverter circuit is constituted by inserting a circuit in which n-type MOSFETs are connected in series between a ground line and a source of a MOSFET of the second power source switch LDSW2. To be more specific, one inverter circuit includes, corresponding to the U phase, the MOSFET(Q11) in which a gate signal G21 is supplied to a gate and a source of a MOSFET of the second power source switch LDSW2 is connected to a drain, and the MOSFET(Q12) in which a drain is connected to the source of the MOSFET(Q11), a gate signal G22 is supplied to a gate, and a ground line is connected to a source. In the same manner, another inverter circuit includes, corresponding to the V phase, the MOSFET(Q13) in which a gate signal G23 is supplied to a gate and the source of the MOSFET of the second power source switch LDSW2 is connected to a drain, and the MOSFET(Q14) in which a drain is connected to the source of the MOSFET(Q13), a gate signal G24 is supplied to a gate, and a ground line is connected to a source. Further, another inverter circuit includes, corresponding to the W phase, the MOSFET(Q15) in which a gate signal G25 is supplied to a gate and the source of the MOSFET of the second power source switch LDSW2 is connected to a drain, and the MOSFET(Q16) in which a drain is connected to the source of the MOSFET(Q15), a gate signal G26 is supplied to a gate, and a ground line is connected to a source. In the respective MOSFETs (Q11 to Q16) which constitute the second inverter circuit 330, a diode element in the direction shown in FIG. 4 is connected between the source and the drain.

A U-phase drive current is taken out from a connection node between the source of the MOSFET(Q11) and the drain of the MOSFET(Q12). A V-phase drive current is taken out from a connection node between the source of the MOSFET (Q13) and the drain of the MOSFET(Q14). A W-phase drive current is taken out from a connection node between the source of the MOSFET(Q15) and the drain of the MOSFET (Q16).

The generation and the processing of gate signal in the second inverter circuit 330 are also substantially equal to the generation and the processing of the gate signal in the first inverter circuit 230 and hence, the explanation of the generation and processing of the gate signal in the second inverter circuit 330 is omitted.

The second switch circuit 340 shown in FIG. 4 is, in the same manner as the first switch circuit 240, constituted of bidirectional switch circuits which are provided corresponding to respective phases of three-phase drive current. The bidirectional switch circuit is constituted of MOSFETs. Further, the second switch circuit 340 includes gate drivers which are provided corresponding to the bidirectional switch circuits of respective phases, and the gate driver generates gate signals for respective MOSFETs which constitute the bidirectional switch circuit.

To be more specific, the bidirectional switch circuit includes two n-type MOSFETs whose sources are connected with each other, wherein a drain of one MOSFET is connected to an output line for a drive current from the second inverter circuit 330 and a drain of the other MOSFET is connected to a motor winding. Here, a common gate signal is supplied to gates of two MOSFETs from the gate driver. Between a source and a drain of each MOSFET, a diode element is connected in the direction shown in FIG. 4. The gate driver which is provided corresponding to each bidirectional switch circuit, in a state where a predetermined power source voltage VL1 is supplied to the gate driver, generates a gate signal such that the MOSFETs which constitute the bidirectional switch circuit are made conductive with each other when a second pump drive control signal PCNT2 is at H level.

The constitution of the bidirectional switch circuit in the second switch circuit 340 is substantially equal to the constitution of the bidirectional switch circuit in the first switch circuit 240 and hence, the explanation of the constitution of the bidirectional switch circuit in the second switch circuit 340 is omitted.

Accordingly, when a second pump drive control signal PCNT2 is at H level, each gate driver in the second switch circuit 340 generates a gate signal such that a gate voltage of the MOSFET has a higher potential than a source voltage. As a result, in the bidirectional switch circuit, in the same manner as the bidirectional switch circuit of the first switch circuit 240, as shown in FIG. 6, when a control part side has a higher potential than a motor winding side, a current flows in the direction DIR1 along the drain, the source and the diode element D1 of the MOSFET (see FIG. 6), while when the control part side has a lower potential than the motor winding side, a current flows in the direction DIR2 along the drain, the source and the diode element D2 of the MOSFET (see FIG. 6).

Here, when the second pump drive control signal PCNT2 is at L level, each gate driver of the second switch circuit 340 generates a gate signal such that a gate voltage of the MOS-FET has a lower potential than a source voltage so that the bidirectional switch circuit can be electrically cut off.

FIG. 8 is an explanatory view of an example where the first and second switch circuits, 240, 340 and the first and second power source switches LDSW1, LDSW2 shown in FIG. 4 are controlled.

Contents of the control shown in FIG. 8 are realized using a first pump drive control signal PCNT1 which the pump drive processing circuit 400 outputs.

That is, when it is detected that the first pump control part 200 is in a normal state by the first processing circuit 210 in response to a detection signal FAIL1, the pump drive processing circuit 400 performs a control such that, in response to a first pump drive control signal PCNT1, the first power source switch LDSW1 of the first pump control part 200 is brought into a conductive state thus supplying a power source voltage from the power source line VL to the first pump control part 200 and, at the same time, the first switch circuit 240 directly outputs a drive signal amplified by the first inverter circuit 230 to motor windings of the auxiliary artificial heart pump 10. Here, the pump drive processing circuit 400 brings the second power source switch LDSW2 of the second pump control part 300 into a cut-off state so as to prevent the supply of a power source voltage from the power source line VL to the second pump control part 300 and, at the same time, the second switch circuit 340 electrically cuts off the electric connection between a signal line through which a drive signal is outputted and the motor windings of the auxiliary artificial heart pump 10 from each other.

On the other hand, when it is detected that the first pump control part 200 is in a failure state by the first processing circuit 210 in response to a detection signal FAIL1, the pump drive processing circuit 400 sets the first pump drive control signal PCNT1 at L level so that the second pump drive control signal PCNT2 is set to H level. Accordingly, the second power source switch LDSW2 of the second pump control part 300 is brought into a conductive state thus supplying a power source voltage from the power source line VL to the second pump control part 300 and, at the same time, the second switch circuit 340 directly outputs a drive signal amplified by the second inverter circuit 330 to motor windings of the auxiliary artificial heart pump 10. Here, the first power source switch LDSW1 of the first pump control part 200 is brought into a cut-off state so as to prevent the supply of a power source voltage from the power source line VL to the first pump control part 200 and, at the same time, the first switch circuit 240 electrically cuts off the electric connection between a signal line through which a drive signal is outputted and the motor windings of the auxiliary artificial heart pump 10 from each other.

In this embodiment, the first and second inverter circuits 230, 330 which have a signal power amplification function are liable to be damaged by an overvoltage or an overcurrent. Particularly, with respect to modes in which a failure occurs in the inverter circuit, most of failures occur in a short-circuiting mode where the inverter circuit is short-circuited with motor windings, a power source or a ground line and hence, even when the auxiliary artificial heart pump 10 is connected to the pump control part on a backup side, a situation where a failure state is not overcome is maintained. However, as described above, by providing the switch circuit which cuts off the respective outputs from the control parts or the power source switch which cuts off means for supplying electricity when a failure occurs in the control part (particularly in the inverter circuit), the pump control part of the failure system can be separated from the system and hence, the auxiliary artificial heart pump 10 can be driven continuously using the inverter circuit on a backup side system thus allowing the auxiliary artificial heart pump drive device to exhibit high availability.

Further, a semiconductor switch which is realized by the MOSFET is adopted as the power source switch or the switch circuit and hence, even when a failure occurs in the semiconductor switch per se by any chance, most of failures are failures in a short-circuiting mode whereby the failure does not influence motor driving unless the double failures occur thus largely enhancing reliability of the auxiliary artificial heart pump drive device.

The above-mentioned first and second processing circuits 210, 310 which detect failures occurring in the first and second pump control parts 200, 300 preferably perform the failure detection processing described hereinafter.

The function of the first processing circuit 210 of the first pump control part 200 or the function of the second processing circuit 310 of the second pump control part 300 which performs the detection processing of the failure in this embodiment may be realized by hardware or software. Hereinafter, it is assumed that the function of the first or the second processing circuit 210, 310 is realized by software processing.

Figure 9:
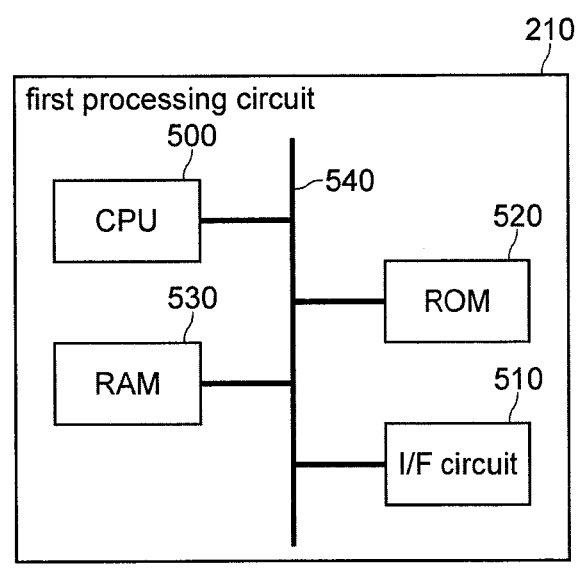
FIG. 9 is a block diagram of a hardware constitutional example of a first processing circuit of a first pump control part according to the embodiment.

FIG. 9 shows a block diagram of a constitutional example of the hardware of the first processing circuit 210 of the first pump control part 200 in this embodiment. Although FIG. 9 shows the constitutional example of the first processing circuit 210, the second processing circuit 310 of the second pump control part 300 may have the same constitution as FIG. 9.

The first processing circuit 210 includes a CPU 500, an I/F circuit 510, a ROM (Read Only Memory) 520, a RAM (Random Access Memory) 530 and a bus 540. The CPU 500, the I/F circuit 510, the ROM 520 and the RAM 530 are electrically connected with each other via the bus 540.

For example, a program for realizing functions of the first processing circuit 210 is stored in the ROM 520 or the RAM 530. The CPU 500 can realize the functions of the first processing circuit 210 based on software processing by reading the program stored in the ROM 520 or the RAM 530 and by executing the processing corresponding to the program. That is, with the use of the CPU 500 which reads the program stored in the ROM 520 or the RAM 530 and performs processing corresponding to the program, the following processing is realized. Here, the RAM 530 is used as a working area for the processing executed by the CPU 500 or is used as a buffer area for the I/F circuit 510 or the ROM 520. The I/F circuit 510 performs input/output interface processing between the first processing circuit 210 and the pump drive processing circuit 400.

Figure 10:
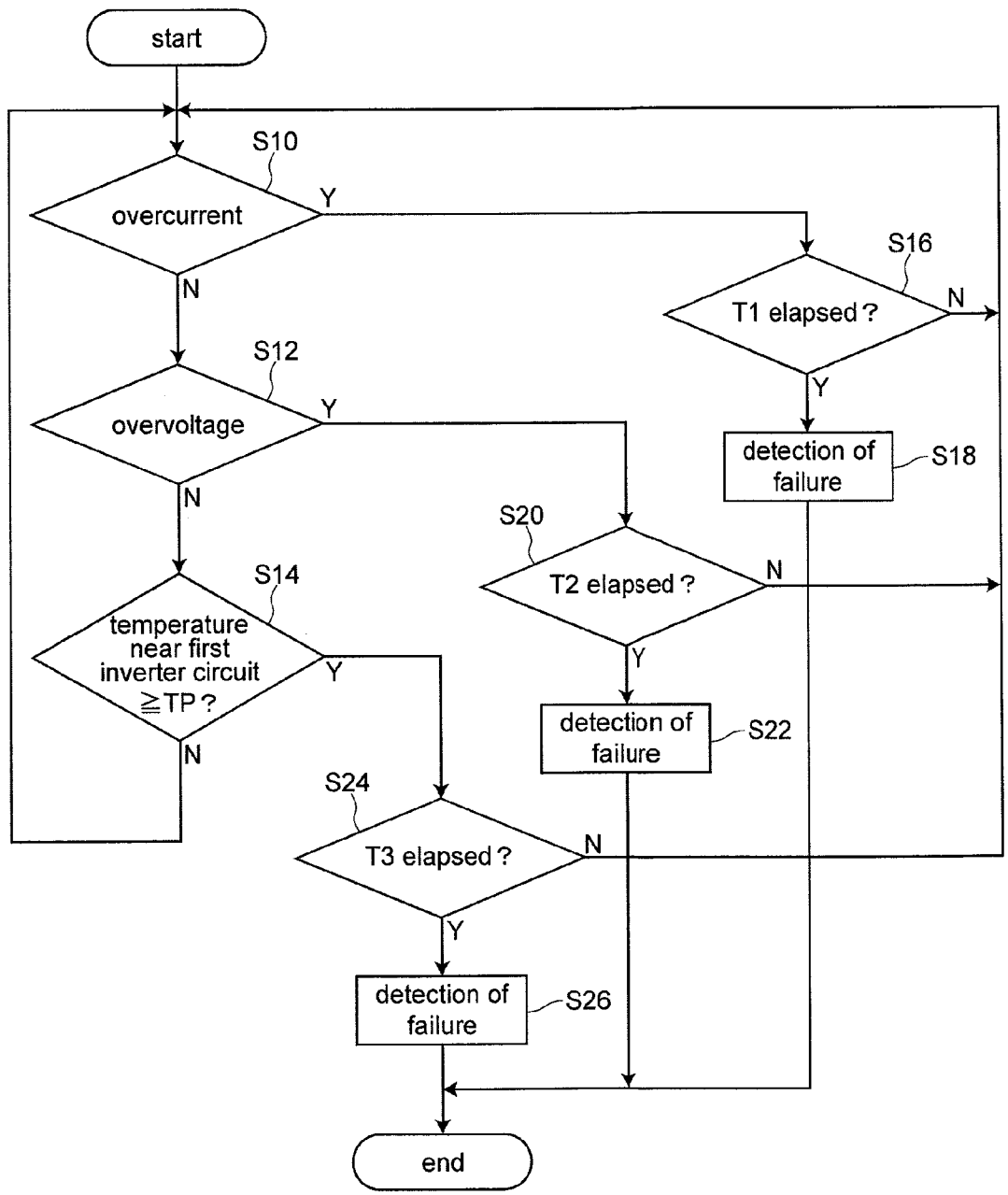
FIG. 10 is a flowchart of a processing example of the first processing circuit shown in FIG. 9.

FIG. 10 is a flowchart showing a flow of a processing example of the first processing circuit 210 shown in FIG. 9. For example, in the ROM 520 or the RAM 530 shown in FIG. 9, a program for realizing the processing shown in FIG. 10 is stored. The CPU 500 reads the program stored in the ROM 520 or the RAM 530 and executes the processing corresponding to the program thus realizing the processing shown in FIG. 10 based on software processing.

The first processing circuit 210 monitors a current $IM_1$ of the power source line VL supplied to the first pump control part 200 via the first power source switch LDSW1, and determines whether or not the current $IM_1$ of the power source line VL is an overcurrent of the power source line VL at predetermined overcurrent detection timing (step S10).

When it is determined that the current $IM_1$ of the power source line VL is not in an overcurrent state in step S10 (step S10: N), the first processing circuit 210 monitors a voltage $VM_1$ of the power source line VL supplied to the first pump control part 200 via the first power source switch LDSW1, and determines whether or not the voltage $VM_1$ of the power source line VL is an overvoltage of the power source line VL at predetermined overvoltage detection timing (step S12).

When it is determined that the voltage $VM_1$ of the power source line VL is not in an overvoltage stage in step S12 (step S12: N), the first processing circuit 210 determines, at predetermined temperature detection timing, whether or not a temperature near the first inverter circuit 230 is a predetermined threshold temperature TP or more based on a sensing result of the first temperature sensor 250 (step S14).

When it is determined that the temperature near the first inverter circuit 230 is not the threshold temperature TP or more in step S14 (step S14: N), the first processing circuit 210 returns to step S10 and continues the monitoring of the respective elements which become failure factors again.

When the overcurrent is detected in the power source line VL at the overcurrent detection timing in step S10 (step S10: Y), the first processing circuit 210 returns to step S10 to wait for a lapse of a predetermined detection period T1, and detects the presence or the non-presence of an overcurrent in the power source line VL again (step S16: N). Accordingly, when the first processing circuit 210 does not detect the overcurrent in the power source line VL during the detection period T1 from the overcurrent detection timing, the first processing circuit 210 performs the detection of another failure factor. On the other hand, when the overcurrent is continuously detected in the power source line VL even after the lapse of the detection period T1 from the overcurrent detection timing, the first processing circuit 210 determines that a failure is detected, notifies the occurrence of a failure to the pump drive processing circuit 400 in response to a detection signal FAIL1 (step S18), and finishes a series of processing (end).

Accordingly, the erroneous detection of an overcurrent in the power source line VL attributed to noises or the like and the detection of a failure attributed to an overcurrent in the power source line VL at a level which does not obstruct the continued operation of the auxiliary artificial heart system can be eliminated and hence, the auxiliary artificial heart system can maintain high availability.

When the overvoltage is detected in the power source line VL at the overvoltage detection timing in step S12 (step S12: Y), the first processing circuit 210 returns to step S10 to wait for a lapse of a predetermined detection period T2, and detects the presence or the non-presence of an overcurrent in the power source line VL again (step S20: N). Accordingly, when the first processing circuit 210 does not detect the overvoltage in the power source line VL during the detection period T2 from the overvoltage detection timing, the first processing circuit 210 performs the detection of another failure factor. On the other hand, when the overvoltage is continuously detected in the power source line VL even after the lapse of the detection period T2 from overvoltage detection timing, the first processing circuit 210 determines that a failure is detected, notifies the occurrence of a failure to the pump drive processing circuit 400 in response to a detection signal FAIL1 (step S22), and finishes a series of processing (end).

Accordingly, the erroneous detection of an overvoltage in the power source line VL attributed to noises or the like and the detection of a failure attributed to an overvoltage in the power source line VL at a level which does not obstruct the continued operation of the auxiliary artificial heart system can be eliminated and hence, the auxiliary artificial heart system exhibits high availability. Further, until the detection period T2 elapses after the overvoltage in the power source line VL is detected at the overvoltage detection timing, the overcurrent in the power source line VL can be detected and hence, it is possible to rapidly switch the system in response to an overcurrent which may become a factor causing more serious failure than the overvoltage.

When it is detected that the temperature near the first inverter circuit 230 is the threshold temperature TP or more at the temperature detection timing in step S14 (step S14:Y), the first processing circuit 210 detects the presence or the non-presence of the overcurrent in the power source line VL again to wait for a lapse of a predetermined detection period T3 (step S24: N). Accordingly, when the first processing circuit 210 does not detect that the temperature near the first inverter circuit 230 is the threshold temperature TP or more during the detection period T3 from the temperature detection timing, the first processing circuit 210 performs the detection of another failure factor. On the other hand, when the first processing circuit 210 detects that the temperature near the first inverter circuit 230 is the threshold temperature TP or more continuously even after the lapse of the detection period T3 from the temperature detection timing, the first processing circuit 210 determines that a failure is detected, notifies the occurrence of a failure to the pump drive processing circuit 400 in response to a detection signal FAIL1 (step S26), and finishes a series of processing (end).

Accordingly, the erroneous detection of the temperature near the first inverter circuit 230 attributed to noises or the like and the detection of a failure attributed to a temperature change at a level which does not obstruct the continued operation of the auxiliary artificial heart system can be eliminated and hence, the auxiliary artificial heart system exhibits high availability. Further, until the detection period T3 elapses after the first processing circuit 210 detects that the temperature near the first inverter circuit 230 is the threshold temperature TP or more at the temperature detection timing, the overcurrent and the overvoltage in the power source line VL can be detected and hence, it is possible to rapidly switch the system in response to an overcurrent and an overvoltage which may become factors causing more serious failures than the temperature.

Figure 11:
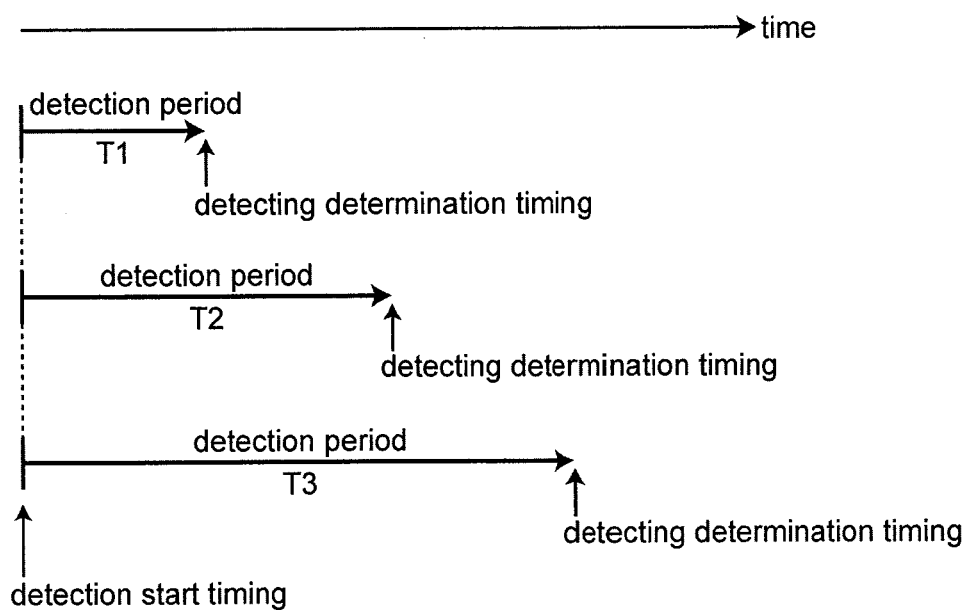
FIG. 11 is an explanatory view of detection periods shown in FIG. 10.

FIG. 11 is an explanatory view showing the detection periods T1, T2 and T3 in FIG. 10. FIG. 11 is provided for explaining the difference among the detection periods T1, T2 and T3 by aligning the detection start timings of the respective detection periods with each other.

In FIG. 10, assuming the overcurrent detection timing as the detection start timing, the period until the detection determination timing at which a failure is detected in step S18 is set as T1 as described above, and this period corresponds to the detection period in which the presence or the non-presence of the failure is detected based on the overcurrent in the power source line VL. In the same manner, assuming the overvoltage detection timing as the detection start timing, the period until the detection determination timing at which a failure is detected in step S22 is set as T2 as described above, and this period corresponds to the detection period in which the presence or the non-presence of the failure is detected based on the overvoltage in the power source line VL. Further, assuming the temperature detection timing as the detection start timing, the period until the detection determination timing at which a failure is detected in step S26 is set as T3 as described above, and this period corresponds to the detection period in which the presence or the non-presence of the failure is detected based on the temperature near the first inverter circuit 230 (first pump control part 200 in the broad meaning).

Here, as shown in FIG. 11, it is desirable that the respective detection periods satisfy the relationship of 0<T1<T2<T3. That is, by performing the failure determination such that the detection period for detecting the overcurrent becomes shortest among three kinds of detection periods, the system can be rapidly changed over in response to the failure factor which is unavoidable and is more serious thus enhancing the availability of the system. Further, by performing the failure determination such that the detection period for detecting the temperature near the first inverter circuit 230 becomes longest among three kinds of detection periods, the order of priority is set low with respect to the countermeasure against the temperature near the first inverter circuit 230 which changes at a long cycle although a failure becomes serious once the failure occurs in this case. By lowering the order of priority with respect to the countermeasure against the temperature near the first inverter circuit 230, the rapid countermeasure can be taken against other failure factors so that the availability of the system is enhanced.

Although the explanation has been made with respect to the first processing circuit 210 in FIG. 9 to FIG. 11, the second processing circuit 310 also has the substantially equal constitution as the first processing circuit 210 and can perform the substantially equal processing as the first processing circuit 210.

[Modification]

In this embodiment, as the drive device which exhibits high reliability and high availability, the explanation has been made with respect to the auxiliary artificial heart pump drive device for driving the auxiliary artificial heart pump in the auxiliary artificial heart system. However, the present invention is not limited to the auxiliary artificial heart pump drive device. For example, the first and second pump control parts 200, 300 and the pump drive processing circuit 400 in the above-mentioned embodiment may be incorporated into a motor drive device (pump drive device) which requires high reliability and high availability.

In this case, the motor drive device (pump drive device) which drives a motor (pump) includes first and second motor control parts arranged in duplexed configuration where the respective motor control parts which control the motor by outputting a drive signal for driving the motor are arranged in duplexed configuration, and each motor control part has a means which electrically cuts off a path through which the above-mentioned drive signal is outputted to the motor when a failure is detected in the motor control part.

Further, in the above-mentioned motor drive device, each motor control part may include a means which stops the supply of electricity to the motor control part when a failure is detected in the motor control part.

Further, in the above-mentioned motor drive device, the means which stops the supply of electricity may be a unidirectional switch circuit which is connected to a power source line through which electricity is supplied to the motor.

Further, in the above-mentioned motor drive device, the unidirectional switch circuit may be constituted of a MOSFET.

Further, in the above-mentioned motor drive device, each motor control part may include a power amplifier which amplifies power of the above-mentioned drive signal and a bidirectional switch circuit which is provided between an output of the power amplifier and the motor, and when the first motor control part is in a normal state, the bidirectional switch circuit of the first motor control part may be set in a conductive state and the bidirectional switch circuit of the second motor control part may be set in a cut-off state, and when the first motor control part is in a failure state, the bidirectional switch circuit of the first motor control part may be set in a cut-off state and the bidirectional switch circuit of the second motor control part may be set in a conductive state.

Further, in the above-mentioned motor drive device, the power amplifier may be an inverter circuit.

Further, in the above-mentioned motor drive device, the bidirectional switch circuit may be constituted of a MOSFET.

Further, in the above-mentioned motor drive device, each motor control part may include a detection circuit for detecting a failure in the motor control part, and may electrically cut off a path through which the drive signal for driving the motor is outputted to the motor from the motor control part when the failure in the motor control part is detected by the detection circuit.

Further, in the above-mentioned motor drive device, the detection circuit may detect a failure in the pump control part using at least one monitoring result out of an overcurrent of a power source line for supplying electricity to the motor drive device, an overvoltage of the power source line and a temperature near the motor control part.

Further, in the above-mentioned motor drive device, assuming a detection period for detecting the presence or non-presence of a failure based on the overcurrent of the power source line as T1, a detection period for detecting the presence or non-presence of a failure based on the overvoltage of the power source line as T2, and a detection period for detecting the presence or non-presence of a failure based on the temperature near the motor control part as T3, it is desirable that the detection periods satisfy the relationship of T1<T2<T3.

Further, a motor system according to the present invention may include a motor and any one of the above-mentioned motor drive devices which drives the motor.

Although the auxiliary artificial heart pump drive device and the auxiliary artificial heart system (the motor drive device and the motor system) according to the present invention have been explained in conjunction with the above-described embodiments heretofore, the present invention is not limited to the above-mentioned embodiments, and the present invention can be carried out in various modes without departing from the gist of the present invention. For example, the following modifications can be considered.

(1) In the above-mentioned embodiments or the modifications thereof, the explanation has been made by taking the auxiliary artificial heart pump (the pump incorporating the motor) having the constitution shown in FIG. 2 as an example. However, the auxiliary artificial heart pump drive device and the auxiliary artificial heart system (motor drive device and motor system) according to the present invention are not limited to the constitution of the auxiliary artificial heart pump (pump).

(2) In the above-mentioned embodiments or the modifications thereof, the explanation has been made by assuming that the pump such as the auxiliary artificial heart pump is the AC motor driven in response to a three-phase drive signal. However, the present invention is not limited to the AC motor. The auxiliary artificial heart pump driven by the auxiliary artificial heart pump drive device according to the present invention (the motor driven by the motor drive device according to the present invention) may include a motor which is driven in response to a drive signal other than the three-phase signal or a DC motor, for example.

(3) In the above-mentioned embodiments or the modifications thereof, the explanation has been made with respect to the case where a failure is detected based on three kinds of failure factors. However, the present invention is not limited to such a case. For example, a failure may be detected based on at least one of the above-mentioned three kinds of failure factors. A failure may be detected based on four or more kinds of failure factors by adding other failure factors to the above-mentioned three kinds of failure factors.

(4) In the above-mentioned embodiments or the modifications thereof, the explanation has been made with respect to the case where the present invention is directed to the auxiliary artificial heart pump drive device and the auxiliary artificial heart system (motor drive device and motor system). However, the present invention is not limited to such devices and systems. For example, the present invention may be directed to a drive method or a failure detection method of the auxiliary artificial heart pump drive device (motor drive device) according to the present invention, a program in which processing steps of the drive method or the detection method for realizing the present invention are described or a recording medium in which the program is recorded.

EXPLANATION OF SYMBOLS

10: auxiliary artificial heart pump
11: drive part
12: pump part
13: impeller
14: pump casing
15: inlet port
16: outlet port
17: mechanical seal part
20: control unit
30: cable
100: auxiliary artificial heart system
200: first pump control part
210: first processing circuit
220: first gate driver
230: first inverter circuit
240: first switch circuit
250: first temperature sensor
300: second pump control part
310: second processing circuit
320: second gate driver
330: second inverter circuit
340: second switch circuit
350: second temperature sensor
400: pump drive processing circuit
500: CPU
510: I/F circuit
520: ROM
530: RAM
540: bus
CONT: auxiliary artificial heart pump drive device
FAIL1, FAIL2: detection signal
GD1, GD2: gate driver
$IM_1$, $IM_2$: current
LDSW1: first power source switch
LDSW2: second power source switch
PONT1: first pump drive control signal
PONT2: second pump drive control signal
PS: power source
$VM_1$, $VM_2$: voltage

The invention claimed is:

1. An auxiliary artificial heart pump drive device for driving an auxiliary artificial heart pump, the pump drive device comprising:
a pump drive processing circuit;
first and second pump control parts arranged in duplexed configuration, each pump control part configured for controlling the auxiliary artificial heart pump by outputting a drive signal to the auxiliary artificial heart pump, wherein said each pump control part has a detection circuit configured to detect a failure state in the pump control part by using at least one monitoring result selected from the group of:
  an overcurrent of a power source line for supplying electricity to the auxiliary artificial heart pump drive device that exists for at least a period of time T1,
  an overvoltage of the power source line that exists for at least a period of time T2, and
  a temperature near the pump control part that exists for at least a period of time T3,
  wherein the relationship T1<T2<T3 is satisfied,
a switch circuit which, when the failure state is detected in the pump control part, is configured to electrically cut off a path through which the drive signal is outputted to the auxiliary artificial heart pump, and
a power source switch which, when the failure state is detected in the pump control part, is configured to stop a supply of electricity to the pump control part,
wherein when a normal state is detected by the detection circuit of the first pump control part, the switch circuit and the power source switch of the first pump control part are set in a conductive state by the pump drive processing circuit and the switch circuit and the power source switch of the second pump control part are set in a cut-off state by the pump drive processing circuit, and
when the failure state is detected by the detection circuit of the first pump control part, the switch circuit and the power source switch of the first pump control part are set in the cut-off state by the pump drive processing circuit and the switch circuit and the power source switch of the second pump control part are set in the conductive state by the pump drive processing circuit.

2. An auxiliary artificial heart pump drive device according to claim 1, wherein the power source switch is a unidirectional switch circuit connected to a power source line for supplying electricity to the auxiliary artificial heart pump drive device.

3. An auxiliary artificial heart pump drive device according to claim 2, wherein the unidirectional switch circuit is constituted of a metal oxide film semiconductor field effect transistor.

4. An auxiliary artificial heart pump drive device according to claim 1, wherein
  each pump control part further includes a power amplifier which is configured to amplify of the drive signal, and
  the switch circuit of each pump control part is a bidirectional switch circuit provided between an output of the power amplifier and the auxiliary artificial heart pump, and
  when the first pump control part is in the normal state, the bidirectional switch circuit of the first pump control part is set in the conductive state and the bidirectional switch circuit of the second pump control part is set in the cut-off state, and
  when the first pump control part is in the failure state, the bidirectional switch circuit of the first pump control part is set in the cut-off state and the bidirectional switch circuit of the second pump control part is set in the conductive state.

5. An auxiliary artificial heart pump drive device according to claim 4, wherein each of the power amplifiers is an inverter circuit.

6. An auxiliary artificial heart pump drive device according to claim 4, wherein the bidirectional switch circuit is constituted of a metal oxide film semiconductor field effect transistor.

7. An auxiliary artificial heart system for assisting the flow of blood in a heart, wherein the auxiliary artificial heart system comprises:
  an auxiliary artificial heart pump, and
  the auxiliary artificial heart pump drive device described in claim 1 for driving the auxiliary artificial heart pump.

* * * * *